(12) United States Patent
Hargrove et al.

(10) Patent No.: US 8,849,681 B2
(45) Date of Patent: Sep. 30, 2014

(54) APPARATUS AND METHOD FOR REMOTE ASSESSMENT AND THERAPY MANAGEMENT IN MEDICAL DEVICES VIA INTERFACE SYSTEMS

(75) Inventors: Jeffrey B. Hargrove, Bancroft, MI (US); Robert M. Ford, Troy, MI (US); Thomas B. Johnson, Boyne City, MI (US)

(73) Assignee: Cerephex Corporation, Los Altos, CA (US)

( * ) Notice: Subject to any disclaimer, the term of this patent is extended or adjusted under 35 U.S.C. 154(b) by 261 days.

(21) Appl. No.: 12/672,509

(22) PCT Filed: Aug. 6, 2008

(86) PCT No.: PCT/US2008/072389
§ 371 (c)(1),
(2), (4) Date: Feb. 6, 2010

(87) PCT Pub. No.: WO2009/021075
PCT Pub. Date: Feb. 12, 2009

(65) Prior Publication Data
US 2011/0196693 A1    Aug. 11, 2011

Related U.S. Application Data

(60) Provisional application No. 60/963,486, filed on Aug. 6, 2007, provisional application No. 61/014,917, filed on Dec. 19, 2007, provisional application No. 61/024,641, filed on Jan. 30, 2008, provisional application No. 61/032,241, filed on Feb. 28, 2008.

(51) Int. Cl.
| | | |
|---|---|---|
| G06Q 10/00 | (2012.01) |
| G06Q 50/00 | (2012.01) |
| A61N 1/372 | (2006.01) |
| G06F 19/00 | (2011.01) |
| G06Q 50/22 | (2012.01) |
| A61N 1/36 | (2006.01) |
| A61B 5/048 | (2006.01) |
| A61B 5/00 | (2006.01) |
| A61B 5/0484 | (2006.01) |
| A61B 5/0476 | (2006.01) |

(52) U.S. Cl.
CPC ........... *A61N 1/37247* (2013.01); *A61B 5/4519* (2013.01); *A61B 5/0484* (2013.01); *G06F 19/3443* (2013.01); *G06Q 50/22* (2013.01); *A61B 5/0476* (2013.01); *A61N 1/36014* (2013.01); *G06F 19/3418* (2013.01); *A61B 5/048* (2013.01)
USPC .................................. 705/3; 705/2; 600/300

(58) Field of Classification Search
CPC . G06Q 50/22; G06F 19/3418; A61N 1/37247
USPC ......................................... 705/2–3; 600/300
See application file for complete search history.

(56) References Cited

U.S. PATENT DOCUMENTS

| | | |
|---|---|---|
| 5,810,747 A | 9/1998 | Brudny et al. |
| 6,168,563 B1 | 1/2001 | Brown |
| 6,418,346 B1 | 7/2002 | Nelson et al. |
| 6,497,655 B1 | 12/2002 | Linberg et al. |
| 6,602,469 B1 | 8/2003 | Maus et al. |
| 6,804,656 B1 | 10/2004 | Rosenfeld |
| 6,856,913 B1 | 2/2005 | Silberstein |
| 6,878,112 B2 | 4/2005 | Linberg et al. |
| 7,058,453 B2 | 6/2006 | Nelson et al. |
| 7,060,031 B2 | 6/2006 | Webb et al. |
| 7,177,675 B2 | 2/2007 | Suffin et al. |
| 7,187,790 B2 | 3/2007 | Sabol et al. |
| 7,231,245 B2 | 6/2007 | Greenwald et al. |
| 2002/0055675 A1 | 5/2002 | Llinas et al. |
| 2003/0204148 A1 | 10/2003 | Lange et al. |
| 2004/0092809 A1 | 5/2004 | DeCharms |
| 2006/0074298 A1 | 4/2006 | Borsook et al. |
| 2006/0247709 A1* | 11/2006 | Gottesman et al. ............. 607/30 |
| 2007/0213600 A1* | 9/2007 | John et al. .................... 600/300 |
| 2007/0250345 A1 | 10/2007 | Walker et al. |
| 2011/0263999 A1* | 10/2011 | Carlson et al. ................ 600/544 |

FOREIGN PATENT DOCUMENTS

| KR | 2000-0054062 | | 9/2000 |
|---|---|---|---|
| WO | 0143631 | A1 | 6/2001 |
| WO | 0143823 | A1 | 6/2001 |
| WO | 2006104846 | A1 | 10/2006 |

OTHER PUBLICATIONS

Jeffrey B. Hargrove, Method and Apparatus for Utilizing Amplitude-Modulated Pulse-Width Modulation Signals for Neurostimulation and Treatment of Neurological Disorders Using Electrical Stimulation, U.S. Appl. No. 11/490,255, filed Jul. 2, 2006.

European Search Report, Application No. 08797311.1-1951, Applicant: Great Lakes Biosciences, LLC, dated Oct. 1, 2013; 11 pages.

\* cited by examiner

*Primary Examiner* — Luke Gilligan

(74) *Attorney, Agent, or Firm* — Reising Ethington P.C.

(57) ABSTRACT

A remote medical assessment and therapy management apparatus comprising a center user interface, a center computer coupleable with the center user interface. The center computer displays information via the center user interface for use in developing a therapeutic prescription and receives therapeutic control inputs from a user. A remote device includes a medical diagnostic instrument for acquiring biophysical data from a patient, a medical therapeutic instrument that provides a therapy to the patient, and a remote computer that receives diagnostic signals from the diagnostic instrument and transmits therapeutic control signals to the therapeutic instrument. A network interface is connected between the first center computer and the remote computer and transmits diagnostic signals from the remote computer to the center computer and control signals from the center computer to the therapeutic instrument via the remote computer.

82 Claims, 9 Drawing Sheets

APPARATUS AND METHOD FOR REMOTE ASSESSMENT AND THERAPY MANAGEMENT IN MEDICAL DEVICES VIA INTERFACE SYSTEMS

CROSS-REFERENCES TO RELATED APPLICATIONS

This application claims priority in and incorporates by reference U.S. Provisional Patent Application Ser. No. 60/963,486 filed 6 Aug. 2007, U.S. Provisional Patent Application Ser. No. 61/014,917 filed 19 Dec. 2007, and U.S. Provisional Patent Application Ser. No. 61/024,641 filed 30 Jan. 2008, and U.S. Provisional Patent Application Ser. No. 61/032,241 filed 28 Feb. 2008.

BACKGROUND OF THE INVENTION

1. Field of the Invention

This invention relates generally to methods and an apparatus for assessment and therapy management of a medical condition, and more specifically to a method of controlling a medical device using electroencephalographic (EEG) measures for assessment and related therapy of a human condition, and more specifically yet, to medical device interface systems.

2. Description of the Related Art

The patent literature provides numerous examples of methods associated with EEG assessment of a human condition and relationships associated with the assessment to providing related therapy, and also teach methods associated with data transfer to and from remote locations.

In United States Patent Application Publication No. 20070250345, Walker et al. describe a method that features the acquisition of assessment information, particularly drawn to polysomnographic information, and associated clinician impressions. Walker further discloses the transfer of this information via, for example, the internet for the development of interpretative reports and prescriptions for treating sleep disorders.

Greenwald et al., in U.S. Pat. No. 7,231,245, discloses a system and method of assessment of a neurological condition using EEG. In U.S. Pat. No. 7,177,675, Suffin et al. disclose yet another EEG-based system that is used in part for selecting therapies.

Suffin's teachings are like many others that anticipate benefits of gathering and using assessment data. But these tend to be limited to such uses as providing feedback to human operators for the purposes of understanding a condition and/or modifying a treatment based on the operator's judgment and action. Other similar teachings include U.S. Pat. No. 7,187,790 in which Sabol et al. disclose a feedback method and system for patient care and training purposes; U.S. Pat. No. 6,804,656 in which Rosenfeld et al. disclose a network-based method of remotely monitoring intensive care units for the purposes of improving critical care; U.S. Pat. No. 6,856,913 in which Silberstein teaches two-way communication between a "central analysis site" and remote sites, where the central site transmits a task to a patient at a remote site and analyzes the patient's response to that task as a way of evaluating the effect of treatment; and U.S. Pat. No. 5,810,747 in which Brudny et al. teach yet another network-based method that permits a remote "supervisor" to manage a patient undergoing "training" to affect a neurological disorder at a remote location.

In addition, the benefits of network-based, e.g., internet-based, communication and monitoring of medical devices is known in the art. For example, in U.S. Pat. No. 6,168,563 Brown teaches the remote monitoring of apparatus used by providers and patients, e.g. blood glucose monitors; and in U.S. Pat. No. 6,602,469 Maus et al. teach a similar monitor and diagnostic device for monitoring blood cholesterol.

Also known in the art are various apparatus for transferring data in and out of implanted medical devices. Examples include the teachings of Nelson et al. (U.S. Pat. Nos. 7,058,453 and 6,418,346); Linberg et al. (U.S. Pat. Nos. 6,878,112 and 6,497,655); and Webb et al. (U.S. Pat. No. 7,060,031). However, the methods taught by these documents are drawn to medical devices that are implanted in human subjects.

None of the systems and methods disclosed in the above documents either disclose or suggest a way for a physician, or any other medical professional or human operator, to assess a patient's neurological condition or administer therapeutic measures to such a patient using a remotely-operated apparatus or without the assessing individual being present or co-located with the patient receiving therapeutic treatment.

SUMMARY OF THE INVENTION

A remote medical assessment and therapy management apparatus is provided that comprises a first center user interface; a first center computer coupleable with the first center user interface and configured to display information via the first center user interface sufficient for a user to assess data associated with a human function or condition and for the user to develop a therapeutic prescription, and further configured to receive therapeutic control inputs from the user; a remote device located remotely from the center and including at least one medical diagnostic instrument configured to acquire biophysical data from a patient, at least one medical therapeutic instrument configured to provide a therapy to a patient, and a remote computer configured to receive diagnostic signals from the diagnostic instrument and to transmit therapeutic control signals to the therapeutic instrument. The apparatus further includes a network interface connected between the first center computer and the remote computer and configured to transmit diagnostic signals from the remote computer to the first center computer and to transmit therapeutic control signals from the first center computer to the therapeutic instrument via the remote computer.

Also provided is a method for remote medical assessment and therapy management. The method includes the steps of providing a center user interface and a center computer configured to display information on the center user interface sufficient for a user to assess data associated with a human condition and for the user to develop a therapeutic prescription, and further configured to receive therapeutic control inputs from a user, providing a remote device located remotely from the center computer and including at least one medical diagnostic instrument configured to acquire biophysical data from a patient, at least one medical therapeutic instrument configured to provide a therapy to a patient, and a remote computer configured to receive diagnostic signals from the diagnostic instrument and to transmit therapeutic control signals to the therapeutic instrument, providing a network interface connected between the center computer and the remote computer and configured to transmit diagnostic signals from the remote computer to the center computer and to transmit therapeutic control signals from the center computer to the therapeutic instrument via the remote computer, and assessing a physical condition of a patient co-located with the remote device by acquiring data pertaining to a physical condition of the patient, transferring the data from the remote device to the center, analyzing at the center the data pertaining to a physical condition of the patient at the remote facility, determining a therapeutic prescription at the center, transferring a therapeutic prescription from the center to the remote device, and providing a therapeutic prescription to the patient using the remote device.

BRIEF DESCRIPTION OF THE DRAWINGS

These and other features and advantages of the invention will become apparent to those skilled in the art in connection with the following detailed description, drawings, photographs, and appendices, in which.

DETAILED DESCRIPTION OF THE INVENTION EMBODIMENT(S)

Figure 1:
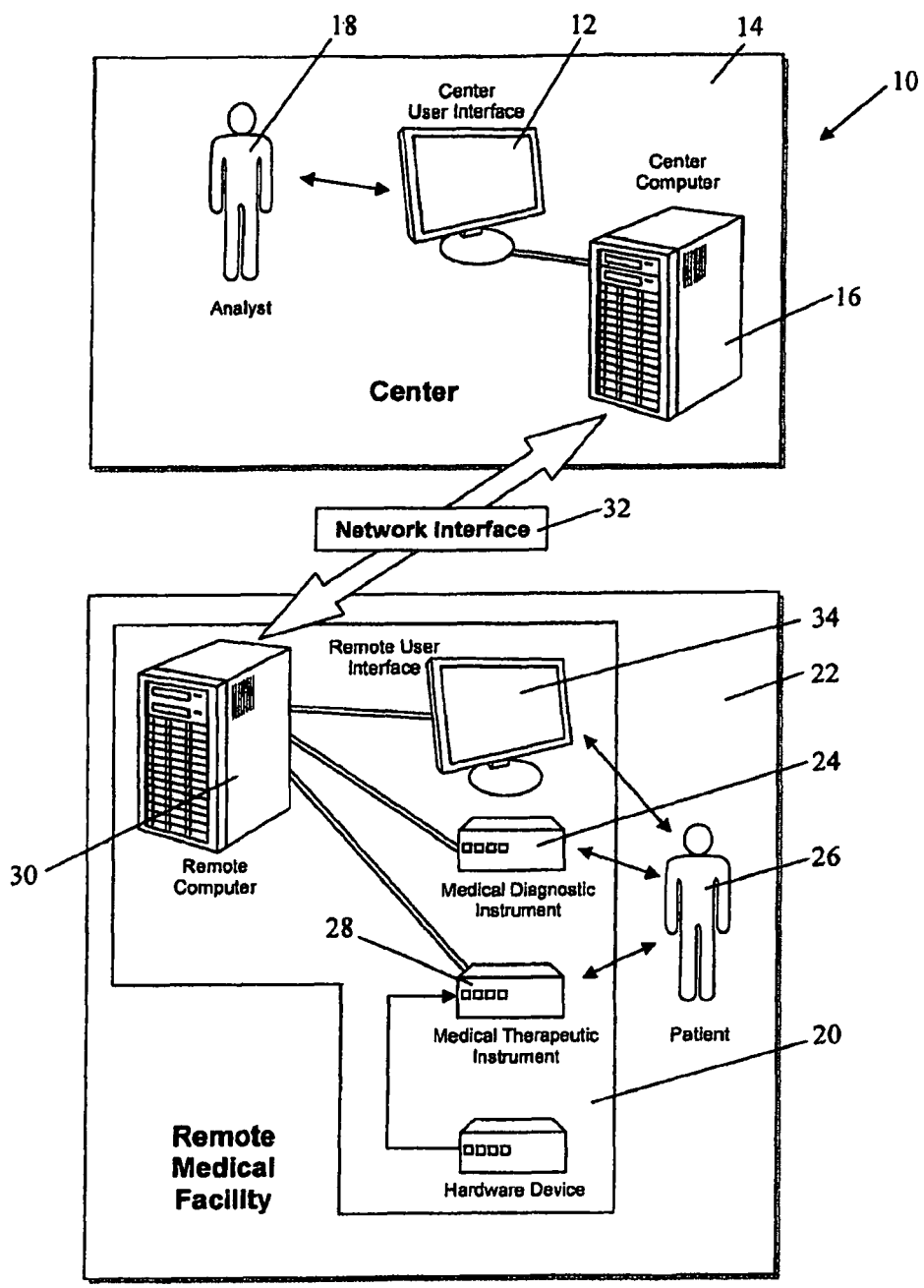
FIG. 1 is a schematic diagram showing a remote medical assessment and therapy management apparatus constructed according to the invention and including a single center location and a single remote facility.

A treatment system is provided that may include, as shown in FIG. 1, one or more localized centers where various functions, processes, and or procedures may be carried out or performed. Those function, processes, and or procedures may include or be associated with one or more of the following: (1) assessment of data associated with a human function or condition; (2) development of a therapeutic prescription; (3) availability and employment of technological expertise associated with a medical instrument, a center computer and a network interface; (4) the performance of a business transaction; (5) operation of an internet website; and (6) availability and employment of medical and research expertise.

According to a first preferred embodiment, and as shown in FIG. 1, the treatment system may include a remote medical assessment and therapy management apparatus 10 comprising one or more center user interfaces 12 located at one or more centers 14 and center computers 16 that may also be located at the or each center 14 and that's programmed to display information via the or each center user interface 12 sufficient for users 18 such as analysts to assess data associated with a human function or condition and for the user to develop a therapeutic prescription. The or each center computer 16 may be further programmed to receive therapeutic control inputs from users via respective center user interfaces 12. The apparatus 10 may also include one or more remote devices 20 located remotely from a center 10 at one or more respective remote locations 22 such as a remote medical facility, the or each comprising any number of diagnostic instruments 24 that may be configured to acquire biophysical data from a patient 26 and/or to assess the physical condition of the patient 26. The or each remote device 20 may also include any number of therapeutic instruments 28 configured to treat a physical condition of the or each patient 26 by providing a therapy to the or each patient 26. The or each remote device 20 may also include a remote computer 30 that may be operationally coupled to the diagnostic instrument 24 and the therapeutic instrument 28. The remote computer 30 may, in turn, be operationally coupled to a means of electronically transmitting data, such as but not limited to a network interface 32 such as a local area network (LAN) or the internet.

The diagnostic instrument 24 of the remote device 20 may comprise a neurodiagnostic apparatus such as an electroencephalogram (EEG) acquisition instrument, and the therapeutic instrument 28 or the remote device 20 may comprise a device for providing electrical stimulation to a patient 26 for treating a physical condition of the patient 26. The diagnostic instrument 24 and the therapeutic instrument 28, preferably a device for providing electrical stimulation for treating a physical condition, may be operationally coupled to the remote computer 30. The remote computer 30 may, in turn, be operationally coupled to the network interface 32. In other words, the network interface 32 may be connected between the center computer 16 and the remote computer 30 and configured to transmit diagnostic signals from the remote computer 30 to the center computer 16 and to transmit therapeutic control signals from the center computer 16 to the therapeutic instrument 28 via the remote computer 30. The remote device may further include a remote user interface 34 operatively coupled to the remote computer 30, the remote computer 30 being configured to accept data inputs regarding the patient's condition via the remote user interface 34, and to communicate the data to the center computer 16 where it may be displayed on the center user interface 12.

Figure 1B:
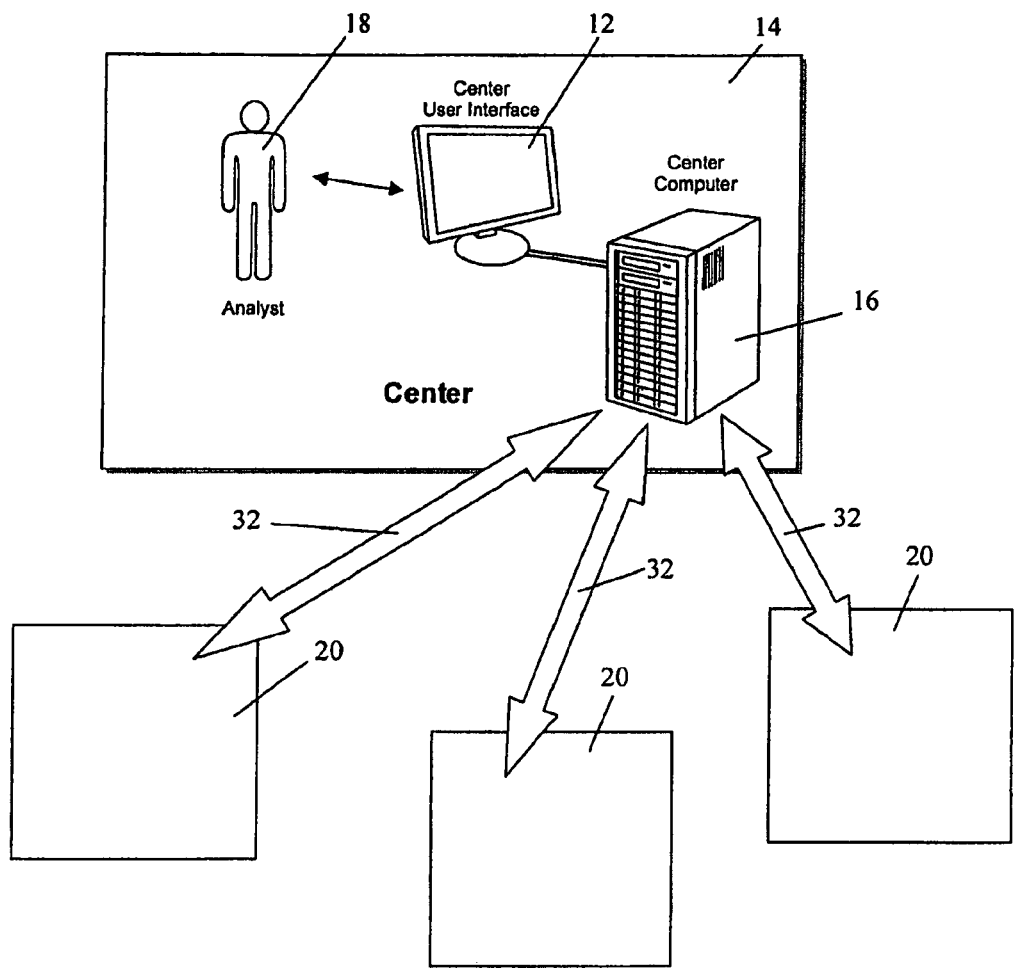
FIG. 1b is a schematic diagram showing a remote medical assessment and therapy management apparatus constructed according to the invention and including a single center location and a plurality of remote facilities.

As shown in FIG. 1b, and as an alternate embodiment, a number of additional remote devices 20 located remotely from a center 14 may be provided, whereupon each remote device 20 may be operationally coupled to a means of electronically transmitting data, such as but not limited to a network interface 32 such as a local area network (LAN) or the internet, and further operationally coupled to a single center 14. Various functions, processes, and or procedures as disclosed above may be carried out or performed at a single center 14 for each individually interfaced remote device 20. Those functions, processes, and or procedures may include or be associated with one or more of the following: (1) assessment of data associated with a human function or condition; (2) development of a therapeutic prescription; (3) availability and employment of technological expertise associated with a medical instrument, a center computer and a network interface; (4) the performance of a business transaction; (5) operation of an internet website; and (6) availability and employment of medical and research expertise. In other words, one or more additional remote devices 20 may be disposed at one or more respective locations remote from the first remote device 20. In other words, the or each additional remote device 20 may comprise a medical diagnostic instrument 24 configured to acquire biophysical data from a patient 26, a medical therapeutic instrument 28 configured to provide a therapy to a patient 26, and a remote computer 30 configured to receive diagnostic signals from the diagnostic instrument 24 and to transmit therapeutic control signals to the therapeutic instrument 28. A network interface 32 may be connected between the center computer 16 and the remote computer 30 of the or each additional remote device 20 and may be configured to transmit diagnostic signals from the remote computer 30 of the or each additional remote device 20 to the center computer 16 and to transmit therapeutic control signals from the center computer 16 to the therapeutic instrument 28 of the or each additional remote device 20 via the remote computer 30 of the or each respective additional remote device 20

Figure 2:
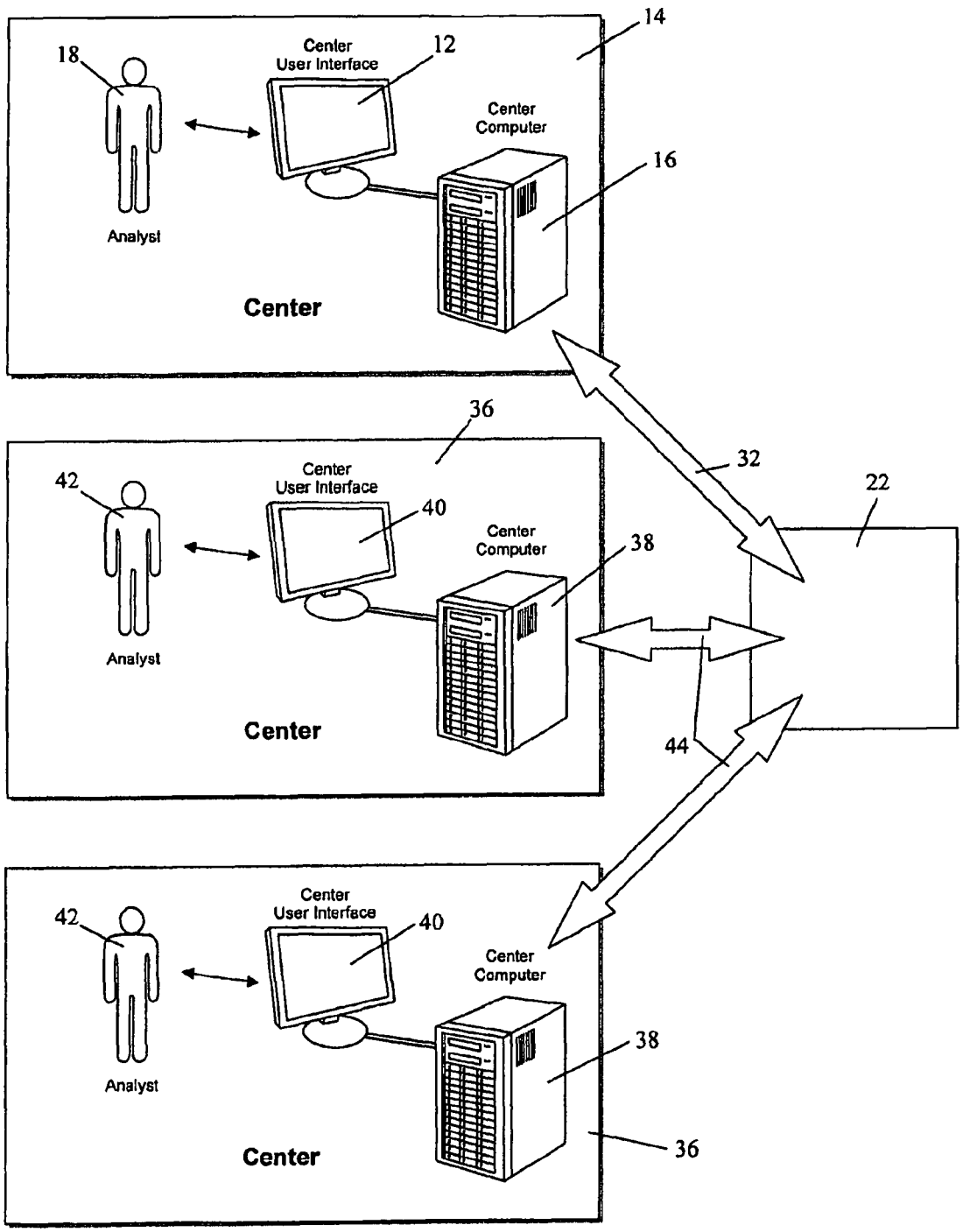
FIG. 2 is a schematic diagram showing a remote medical assessment and therapy management apparatus constructed according to the invention and including a plurality of center locations and a single remote facility.

As shown in FIG. 2, a number of additional localized centers 36 may be provided where there may be located respective center computers 38 and/or center user interfaces 40 as disclosed above as well as physical means and people necessary to facilitate various functions associated with providing medical services with respect to a remote device 20. The medical services provided at one or more of these centers 10 may include, but are not limited to, (1) assessment of data associated with a human function or condition and acquired on a remote device and transmitted to a center; (2) development of a therapeutic prescription to be applied in association with a remote device; (3) provision of technological methods such as support expertise associated with a medical instrument, a computer and a network interface; (4) the performance of a business transaction; (5) operation of one or more internet websites; (6) provision of medical expertise about a physical condition; and (7) provision of research expertise about a physical condition. In other words, additional center user interfaces 40 may be disposed at respective centers 36 remote from the first center user interface 12 and from each other. Additional center computers 38 may be coupleable with the respective additional center user interfaces 40 and configured to display information via the respective additional center user interfaces 40 sufficient for users 42 to assess data associated with a human function or condition and for the user to develop a therapeutic prescription, and further configured to receive therapeutic control inputs from the users 42. Additional network interfaces 44 may be connected between the respective additional center computers 38 and the remote computer 30 and configured to transmit diagnostic signals from the remote computer 30 to the respective additional center computers 38 and to transmit therapeutic control signals from the respective additional center computers 38 to the therapeutic instrument 28 via the remote computer 30.

The or each remote device 20, the or each center computer 16, 38 and the or each network interface 32, 44 may be configured to use any one or more methods known in the art for providing the electronic transfer of data over a network.

Provision may also be made for an internet website to be used by a physician or similarly qualified person of medical expertise for the purposes of providing or receiving information and data about a physical condition of a patient using a remote device. Provision may further be made for the internet website to be accessed and used on a computational means such as a computer operating any one of a number of standard internet browser software programs.

Provision may also be made for persons associated with a patient suffering from a particular physical condition and using a remote device, to use an internet website for the purposes of providing or receiving information and data about the physical condition of the patient using the remote device. Provision may further be made for the internet website to be accessed and used on a computational means such as a computer operating any one of a number of standard internet browser software programs.

Figure 3:
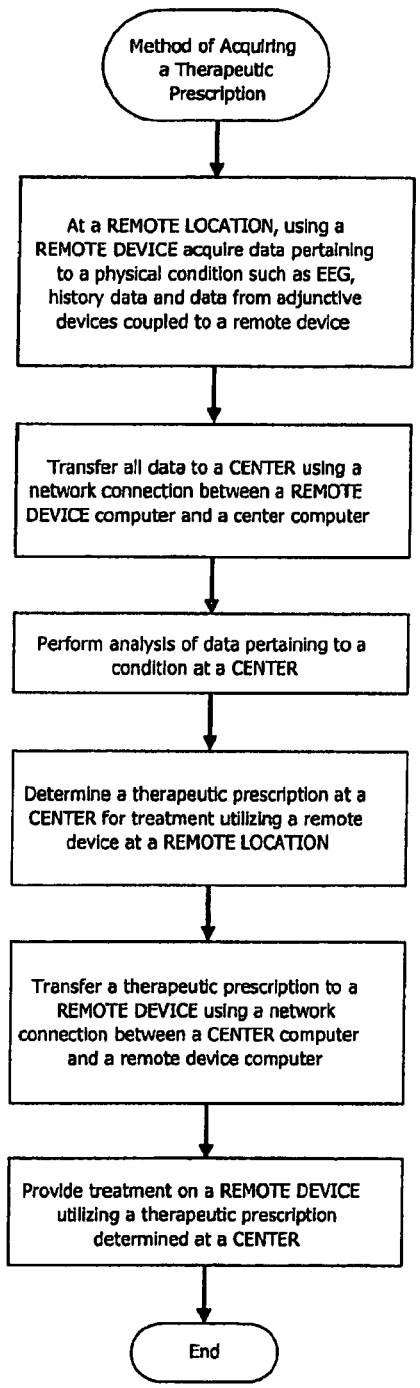
FIG. 3 is a flow chart showing a method of acquiring a therapeutic prescription according to the invention.

As shown in FIG. 3, the treatment system may also include a method of acquiring a therapeutic prescription. This method may include interactions between a center and a remote device for the purpose of treating a physical condition of a patient using the remote device, which may include (1) at a remote location, using a remote device to acquire data pertaining to a physical condition of a patient, e.g., EEG, history data, and/or data from adjunctive devices coupled to a remote device, (2) transferring the data to a center using a network connection between a remote device computer and a center computer, (3) performing analysis of the data, (4) determining a therapeutic prescription at the center for treatment of the patient using a remote device at the remote location, (5) transferring a therapeutic prescription to the remote device using the network connection between the center computer and the remote device computer (5) and providing treatment on the remote device using the therapeutic prescription determined at the center.

Figure 4:
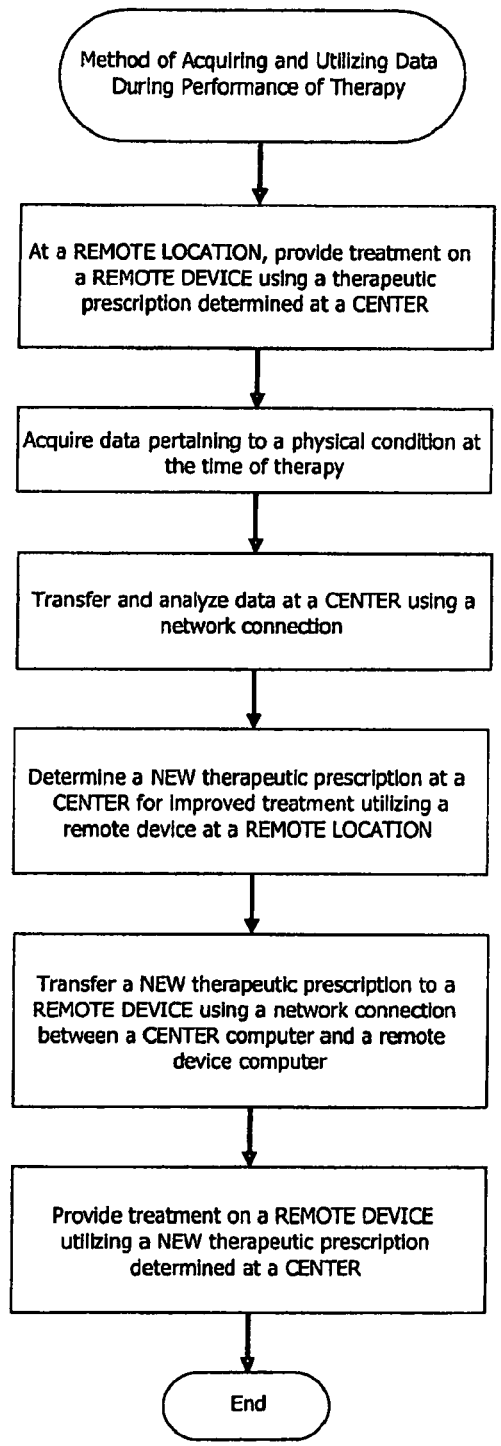
FIG. 4 is a flow chart showing a method of acquiring and using data during the performance of a therapy according to the invention.

As shown in FIG. 4, the treatment system may also include a method of acquiring and using data during the performance of a therapy. This method may include interactions between a center and a remote device for the purpose of treating a physical condition of a patient using the remote device, which may include (1) provision of therapy to the patient using a remote device and further using a therapeutic prescription determined at a center and transferred to the remote device, (2) acquisition of data pertaining to a physical condition of the patient and taken at or near the time of therapy, (3) transferring the data from a remote device to a center, (4) performing analysis of the data pertaining to a physical condition of the patient at a center, (5) determining a new therapeutic prescription at a center, (6) transferring a new therapeutic prescription from a center to a remote device, and (7) providing a new therapeutic prescription to the patient using the remote device.

Figure 5:
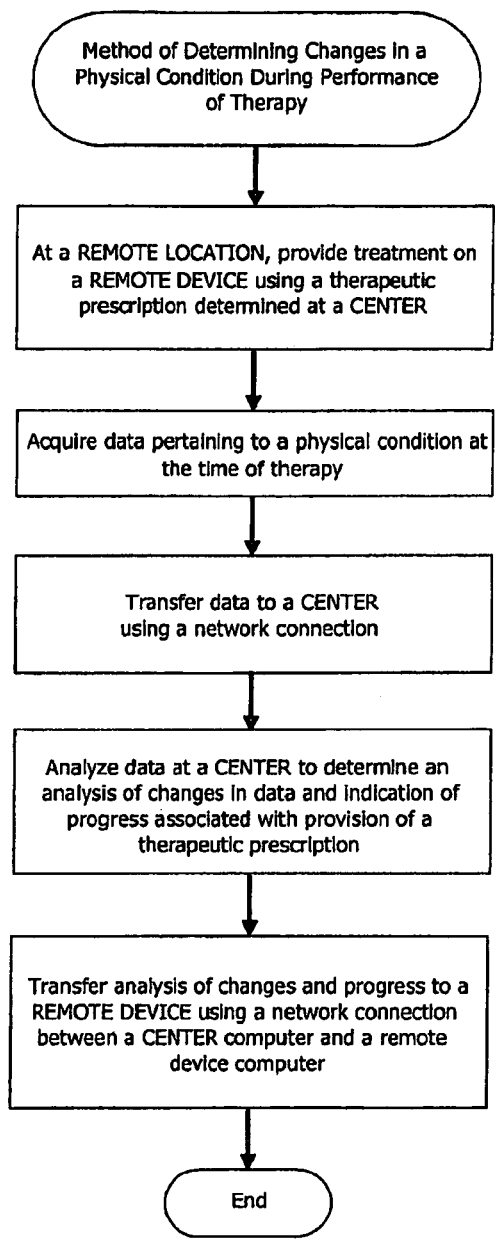
FIG. 5 is a flow chart showing a method of determining changes in a patient's physical condition during performance of a therapy according to the invention.

As shown in FIG. 5, the treatment system may also include a method of determining changes in a physical condition of a patient during performance of a therapy on the patient. This method may include interactions between a center and a remote device for the purpose of treating a physical condition of the patient using the remote device, which may include (1) provision of therapy to a patient using a remote device and further using a therapeutic prescription determined at a center and transferred to the remote device, (2) acquisition of data pertaining to a physical condition of the patient and taken at or near the time of therapy, (3) transferring the data from a remote device to a center, (4) performing analysis of the data pertaining to a physical condition of the patient at a center, (5) determining an analysis of changes in the data over time and associating the analysis of changes with progress toward treating a physical condition of the patient using the remote device, and (6) transferring the analysis of changes and progress to a remote device.

Figure 6:
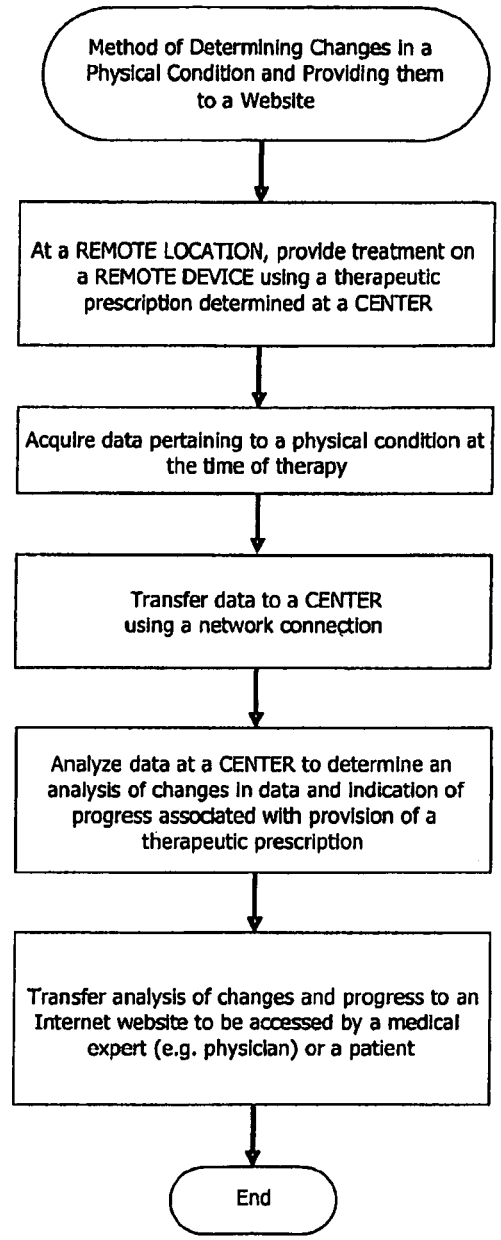
FIG. 6 is a flow chart showing a method of determining changes in a patient's physical condition and providing an analysis of those changes to an interne website according to the invention.

As shown in FIG. 6, the treatment system may also include a method of determining changes in a physical condition of a patient and providing data concerning those changes to a website. This method may include interactions between a center and a remote device for the purpose of treating a physical condition of the patient using the remote device, which may include (1) provision of therapy to the patient using a remote device and further using a therapeutic prescription determined at a center and transferred to the remote device, (2) acquisition of data pertaining to a physical condition of the patient and taken at or near the time of therapy, (3) transferring the data from a remote device to a center, (4) performing analysis of the data pertaining to a physical condition of the patient analyzed at a center, (5) determining an analysis of changes in the data over time and associating the analysis of changes with progress toward treating a physical condition of the patient using the remote device, and (6) transferring the analysis of changes and progress to an internet website.

Figure 7:
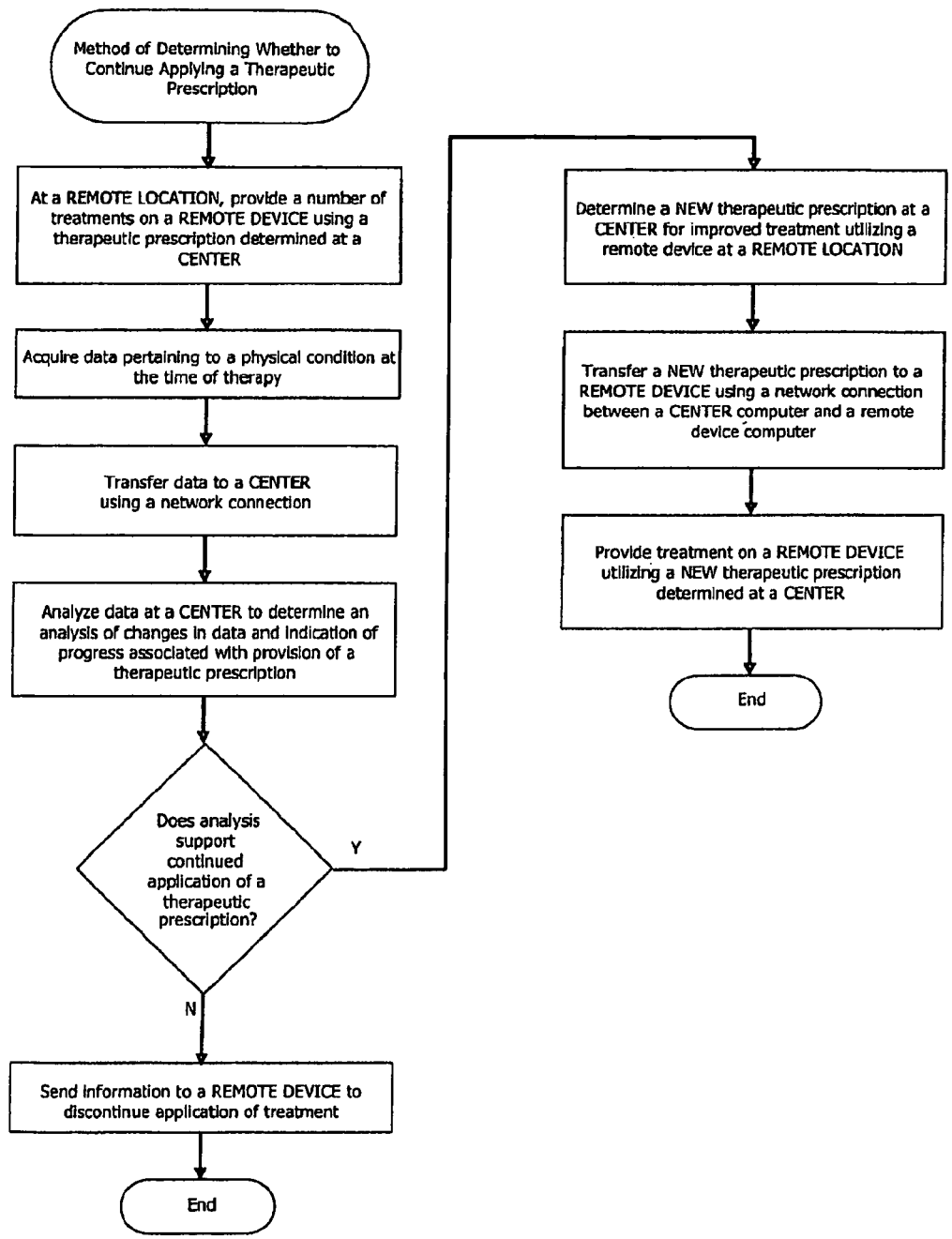
FIG. 7 is a flow chart showing a method of determining whether to continue applying a therapeutic prescription according to the invention.

As shown in FIG. 7, the treatment system may also include a method of determining whether to continue applying a therapeutic prescription to a patent. This method may include interactions between a center and a remote device for the purpose of assessing a physical condition of the patient after a number of applications of a therapy has taken place on the patient using the remote device, which may include (1) acquisition of data pertaining to a physical condition, (2) transferring the data from a remote device to a center, (3) performing analysis of the data pertaining to a physical condition of the patient analyzed and/or treated at a center, and either (3.1) determining a therapeutic prescription at a center, (3.2) transferring a therapeutic prescription from a center to a remote device, and (3.3) providing a therapeutic prescription to a patient using the remote device, or (3.4) determining if further therapeutic intervention is indicated.

The treatment system may also include a process of establishing initial relationships and business capability involving a remote device, a center, a physician or similarly qualified person of medical expertise, and persons associated with the use of a remote device; for providing medical services including but not limited to diagnostic assessment and providing a therapeutic prescription. This process begins with an initial establishment of network communication between a center and a remote device for the purposes of making transactions including those related to providing a medical service, a business service, or a technical support service; and to create a unique remote device identification number to be used by both the remote device and a center in association with related transactions.

The establishment of initial relationships and business capability may also include establishing communication between persons at a center and persons at a location of a remote device for the purposes of making transactions including those related to providing a medical service, a business service, a financial service, or a technical support service; the communication optionally including but not being limited to telephone communications, e-mail, instant messaging and other forms of written, verbal or in-person communication.

The establishment of initial relationships and business capability may further include providing one or more persons who are co-located with a remote device, with an initial inventory of consumable supplies usable by a remote device for the provision of medical services such as acquisition of biophysical measures and provision of a therapeutic prescription; setting preferred inventory re-order points; and providing any number of means of monitoring inventory of the consumable supplies and means of communicating a need to acquire additional inventory when the re-order points have been achieved. The communication may take place between persons at a location of a remote device and persons at a center.

The establishment of initial relationships and business capability may further include creating a user account on a remote device for a patient with a physical condition, where the user account may include the patient's name, a unique user number, information related to providing medical services including assessing and treating a physical condition, and history information associated with assessing and treating a physical condition. The user account may be provided for use at both a remote device and at a center.

The establishment of initial relationships and business capability may further include creating an internet website access account on (1) a website that transacts information and data to and from a patient using a remote device for treatment of a physical condition; and on (2) a website that transacts information and data to and from a physician or similarly qualified person of medical expertise about a physical condition of a patient using a remote device.

The process may also include providing information about a patient or subject and a physical condition suffered by the subject. This may include the use of a remote device to assess elements of a physical condition of a human subject, and may include but is not limited to including the acquisition of information provided by the subject, by other persons associated with the subject, or by a physician or similarly qualified person of medical expertise. Acquisition of the information may be accomplished through interface means such as the use of software interfaces on computer on a remote device, and the manual input of information by a patient using the remote device.

The provision of information about a subject and a physical condition may include the use of an internet website to assess elements of a physical condition of a human subject, and may include but is not limited to including the acquisition of information provided by the subject, provided by other persons associated with the subject, or provided by a physician or similarly qualified person of medical expertise. Acquisition of the information may be accomplished through the use of software interfaces such as an internet browser.

The provision of information about a subject and a physical condition may include the use of a remote device to assess elements of a physical condition of a human subject, and may include but is not limited to the use of diagnostic or assessment instruments either integral or operationally coupled to a remote device, and to the acquisition of measures including, but not limited to biophysical measures provided by the instruments.

The provision of information about a subject and a physical condition may include the use of an internet website to assess elements of a physical condition of a human subject, and may include but is not limited to the use of diagnostic or assessment instruments either integral or operationally coupled to a computer further operationally coupled to an internet website, and to the acquisition of measures provided by the instruments.

The provision of information about a subject and a physical condition may include the use of an interne website to acquire an inquiry from a user for the purpose of determining the closest physical location of a remote device to a person making the inquiry, and may further be used to provide information about the physical location to a center whereupon a determination of the closest physical location is made, and may further be used to provide the determination to the user.

The provision of information about a subject and a physical condition may include the use of an interne website to acquire data and information from a user for the purpose of assisting medical and business services associated with a center and a remote device, where the data and information may include but are not limited to demographic data, medical history data, overall health data, symptom data, other information that may be a factor in the pathology of a physical condition, information pertaining to the quality of services, information pertaining to the scheduling of services, educational information, and information pertaining to a financial transaction.

The provision of information about a subject and a physical condition may include the use of a remote device to acquire data and information from a user for the purpose of assisting medical and business services associated with a center and a remote device, where the data and information may include but are not limited to demographic data, medical history data, overall health data, symptom data, other information that may be a factor in the pathology of a physical condition, information pertaining to the quality of services, information pertaining to the scheduling of services, educational information, and information pertaining to a financial transaction.

The process of providing information about a subject and a physical condition may include electronically transferring to a center data and information gathered or acquired on a remote device or an internet website about a subject's physical condition. Upon receipt at a center, the data and information may be placed into any number of databases with at least one database being specific to the subject. Further, the data and information may be placed into a number of electronic files to be used by third-party software for the process of analyzing aspects of the data as it relates to a physical condition.

The process may further include analyzing and assessing data and information about a subject's physical condition at a center. Analyzing and assessing may include providing to a physician or similarly qualified person of medical expertise data and information received at a center about a subject's physical condition. Provision may be made at a center for the data and information to be used by the physician or similarly qualified person of medical expertise for purposes including but not limited to diagnosing aspects of a physical condition, assessing the extent or severity of a physical condition, determining a therapeutic prescription for treating a physical condition on a remote device, assessing changes in a physical condition as a result of providing a therapeutic prescription on a remote device, and making subsequent adjustments to a therapeutic prescription for the purposes of optimizing a treatment outcome on a remote device.

The analysis and assessment of data and information may include analyzing communicated data, including biophysical measures acquired by instruments integral to or operationally coupled to a remote device and associated with a physical condition, at a center and for the purpose of determining a therapeutic prescription.

The assessment of data may include assessing EEG data collected by a remote device and transferred to a center. The assessment of EEG data may include mathematical methods known in the art for analyzing a patient's EEG using one or more methods such as voltage analysis, current analysis, voltage and current analysis, frequency spectrum analysis using Fast Fourier analysis, frequency spectrum analysis using a wavelet analysis method, frequency spectrum analysis using absolute power analysis method, frequency spectrum analysis using relative power analysis method, frequency spectrum analysis using phase analysis method, frequency spectrum analysis using coherence analysis method, frequency spectrum analysis using amplitude symmetry analysis method, and/or localization of electrical activity in the brain using inverse EEG computation analysis.

The analysis and assessment of data and information may include the determination of statistical significance with respect to deviation from various populations of people including, but not limited to a population of healthy normal individuals and a population of individuals suffering from a same or similar physical condition as a subject.

The analysis and assessment of data and information may further include the use of any number of third party software programs at a center to aid in the assessment of the data and information.

The analysis and assessment of data and information may further include the use of the data and information for the purposes of supporting a first diagnosis made by a physician or similarly qualified person of medical expertise, or providing evidence for a differential diagnosis, or discovering contraindications to the use of a remote device for providing a therapeutic prescription.

The analysis and assessment of data and information may also include provision of various means at a center for determining contraindications to the use of a remote device for providing a therapeutic prescription, where the means may include but are not limited to comparison of data and information provided by (1) a patient seeking a therapeutic prescription on a remote device, or (2) other persons associated with the patient, or (3) a physician or similarly qualified person of medical expertise, or (4) measurements made by instruments operationally coupled to a remote device; the comparison being made between the data and information and contraindications known at a center, and where the determining of a contraindication may be made when the comparison yields a finding of at least one similarity between the data and information and the known contraindications.

Figure 8:
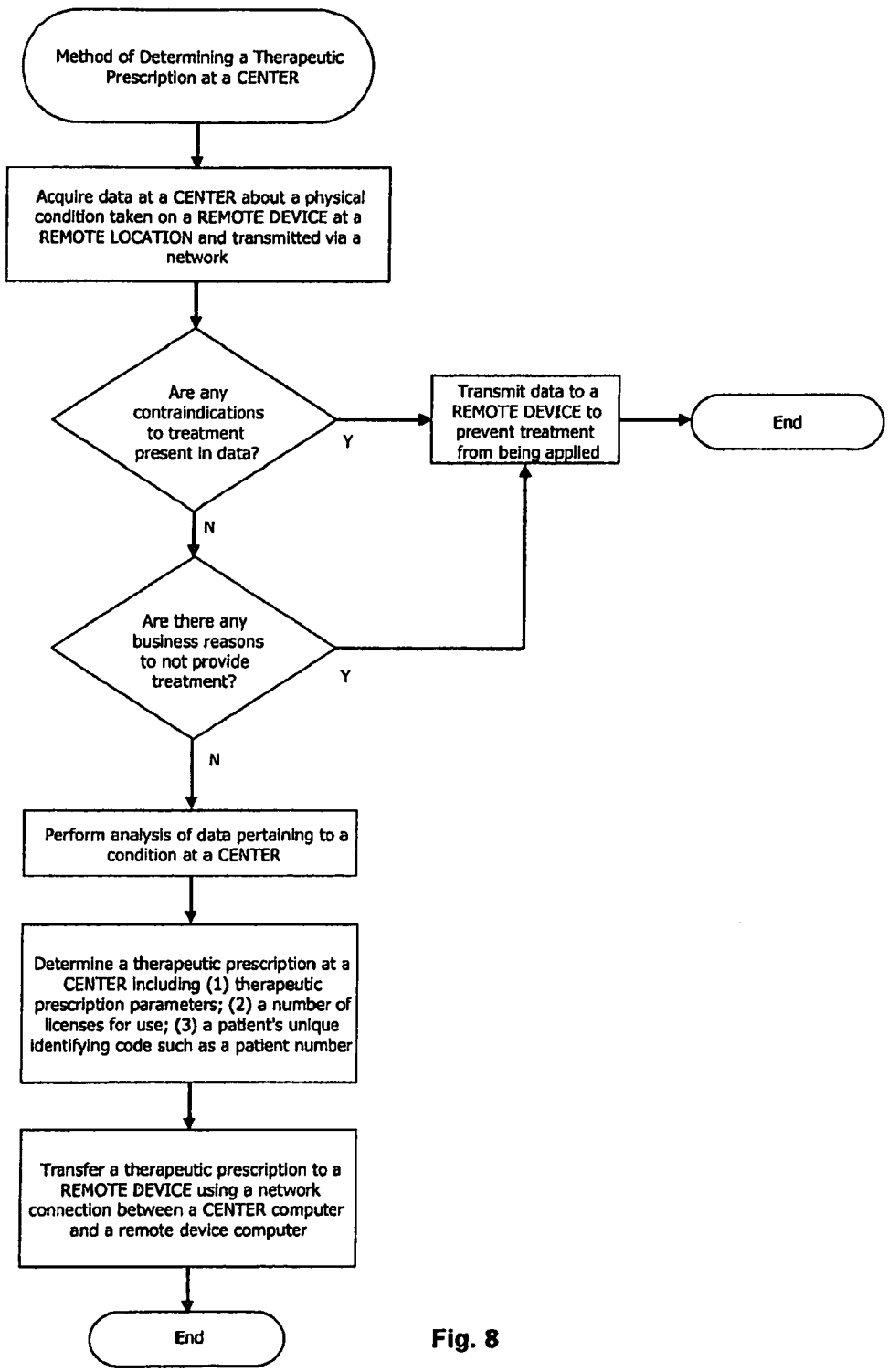
FIG. 8 is a flow chart showing a method of determining a therapeutic prescription at a center according to the invention.

As shown in FIG. 8, the process may further include determining a therapeutic prescription for treating a subject's physical condition at a center, and communicating the therapeutic prescription to a remote device. This may include (1) determining if any contraindications exist based on communicated data; (2) analyzing biophysical measures of a patient with a physical condition for the determination of therapeutic prescription parameters, most preferably associated with affecting the biophysical measures in a beneficial way; (3) creating a data file containing the therapeutic prescription parameters, a number of licenses for use (i.e. a number of allowed applications of a therapy for a patient on a remote device), the user number of a patient using a remote device and the identification number of the remote device; and (4) communicating the data file from a center to a remote device via network interface.

The determination of a therapeutic prescription may involve the use of aforementioned analysis of EEG measures to determine parameters of an electrical stimulation signal used to treat a physical condition, and using the parameters of an electrical stimulation signal as part of a therapeutic prescription.

The process may further include transferring information and data between a remote device and a center, for the purposes of providing a medical service, a business service, or a technical support service. Provision may preferably be made for a period of time where connectivity between a remote device and a center is established using electronic means such as operational coupling to a network such as a LAN or the internet. Software means may preferably be provided for the transfer of data between a remote device and a center when the connectivity is established, where the transfer may be accomplished by any number of data transfer means commonly known in the art.

The transfer of information and data may include a center posting files and data to a location such as an FTP site, where a remote device may download the files and data upon connection to a network or at a preset scheduled time after connection to a network.

The transfer of information and data may further include a center electronically notifying persons associated with a remote device of the status of data transfers and transactions involving a patient with a physical condition using the remote device. The notification may be accomplished by any of the aforementioned means of communicating between persons associated with a center and persons associated with a remote device.

The transfer of information and data may further include the transfer of data from a center to a repository of data for use in research purposes including the building of databases of patient information subsequently used for statistical comparison related to diagnosis and assessment of a physical condition.

The transfer of information and data may further include the use of a means of transmitting information supporting a first diagnosis or providing evidence for a differential diagnosis from a center to a physician or similarly qualified person of medical expertise for use in the overall treatment of a patient with a physical condition.

The transfer of information and data may further include transmitting data from a center to a remote device, where the data may be interpreted by the remote device to prevent a therapeutic prescription from being delivered if a contraindication to use of the remote device is discovered or if requisite information that is needed to determine if a contraindication exists is not present. Further, the process may provide for the prevention of use of a remote device for providing a therapeutic prescription if the contraindications are detected or if the requisite information is not present.

The process may further include the performance of a medical service on a remote device. This performance of a medical service may include providing a therapeutic prescription to a person on a remote device by (1) authenticating the identify of the person; (2) using software applications to provide the person a means of reporting the status of a set of symptoms; (3) using software to automatically select a therapeutic prescription provided for the person by a center; (4) providing the therapeutic prescription; (5) acquiring additional data including biophysical measures pertaining to a patient's physical condition; and (6) communicating the additional data to a center via network connection.

The step of performing a medical service may include providing for assessment at a center of data associated with providing a therapeutic prescription on a remote device, which may include (1) receiving the data from a remote device via network connection; (2) performing various analyses on the data including mathematical analysis and statistical analysis; (3) using the analyses to quantify the status of symptoms associated with a physical condition; (4) using the analyses to create a new therapeutic prescription for the purpose of improving therapeutic effect; (5) communicating the new therapeutic prescription to a remote device; (6) communicating the analyses to an internet website used by a physician or similarly qualified person of medical expertise; and (7) communicating the analyses to an internet website used by a patient with a physical condition.

The performance of a medical service may include authenticating that a patient using a remote device for provision of medical services is the same as a person bearing a certain user name and account. The authentication may be accomplished by software means on a remote device or by interaction with a person at a location of a remote device such as a physician or similarly qualified person of medical expertise.

The performance of a medical service may include permitting the use of a therapeutic prescription on a patient with a physical condition on a remote device only if a number of licenses associated with the patient's user account is greater than zero.

The performance of a medical service may include use of any number of software applications on a remote device to provide a patient having a physical condition a means of inputting information and data about their symptoms and condition, and further communicating the information and data to a center.

The performance of a medical service may include having a patient use software applications on a remote device for inputting information and data about their symptoms and condition at a time of providing a therapeutic prescription, and further communicating the information and data to a center.

The performance of a medical service may include providing adjunctive software and hardware devices that operationally couple to a remote device and using such adjunctive software and hardware devices to augment treatment of a patient with a physical condition. The adjunctive software and hardware devices may include, but are not limited to other medical instruments used for assessing and treating a physical condition.

The performance of a medical service may include providing adjunctive software and hardware devices that operationally couple to a remote device and using such adjunctive software and hardware devices to augment treatment of a related or unrelated coexisting physical condition in a patient with a physical condition. The adjunctive software and hardware devices may include, but are not limited to other medical instruments used for assessing and treating a physical condition.

The performance of a medical service may include using software on a remote device for the purposes of educating or counseling a patient about a physical condition. The software may include but is not limited to software that provides a written narrative, audio and/or video presentations involving education or counseling of a patient about a physical condition.

The performance of a medical service may include various applicable aspects of the diagnosis and treatment methods disclosed in U.S. Provisional Patent Application Ser. Nos. 60/963,486; 61/014,917; 61/024,641; and/or 61/032,241 and or U.S. patent application Ser. No. 11/490,255.

The process may also include managing a remote device via communication means between a remote device and a center. Preferably, software applications run on a remote device monitor and collect data about various performance aspects of the remote device. The performance aspects may include but are not limited to proper use of a remote device, integrity of measures being taken by medical instruments integral to a remote device, and data indicating the operational status of a remote device. Preferably, data about performance aspects of a remote device is electronically communicated to a center via network connection, where it is further used at a center for the management of the remote device.

The management of a remote device may include providing a means to automatically communicate data between a center and a remote device for detection and repair of faults and associated errors that limit functionality of the remote device. This managing step may also include providing for communication of information pertaining to faults and associated errors that limit functionality of the remote device to persons located at a remote device.

Managing a remote device may also include returning data from a center to a remote device and having software on a remote device use the data for the purposes of correcting or repairing faults and associated errors that limit functionality of the remote device.

Managing a remote device may also include the provision by a center for the transfer of data used to upgrade software and firmware associated with various functions of the remote device.

Managing a remote device may also include providing for the determination and transfer of data regarding faults and associated errors; for the transfer of the data to a center via a network; and for the use of the data in facilitating technical support between persons at a center and a remote device.

Managing a remote device may also include provision for the detection of use or performance problems associated with a remote device, such as but not limited to the detection of a low battery, detection of low supplies and detection of poor data integrity; communication of data associated with the problems to a center via a network; a communication of the problems to persons at a location of a remote device.

Managing a remote device may include provision for analysis at a center of all communicated data from biophysical measures, most preferably EEG data, associated with a medical device; further used for the purposes of assuring integrity of the biophysical measures; and further to the communication of a finding of measurement integrity to a person at a location of a remote device.

Also provided is a process of transacting ongoing business and operational capability between a remote device, a center, a patient using a remote device, and persons associated with providing medical services on a remote device. Such transactions may preferably include, but are not limited to generating financial transactions between a center and a remote device in association with the provision of medical services.

The process of transacting ongoing business and operational capability may include generating reports based on assessment of data at a center; transmitting the reports from a center to a person at a location of a remote device, most preferably a physician or similarly qualified person of medical expertise, and most preferably yet transmitting the reports to an internet website used by the person at a location of a remote device—to be used further for the purposes of completing a financial transaction, and in particular for the purpose of enhancing Level of Service pertaining to an insurer's reimbursement.

The process of transacting ongoing business and operational capability may include the use of data transmitted from a remote device to a center for the performance of administrative activities associated with providing a medical service on a remote device.

The process of transacting ongoing business and operational capability may include provision for the use of data transmitted from a remote device to a center, for quality and reliability monitoring associated with providing a medical service on a remote device.

The process of transacting ongoing business and operational capability may include providing for the secure transfer of data between a remote device, a center, and associated internet websites; where the secure transfer may be accomplished by any number of means of secure data transfer known in the art.

The process of transacting ongoing business and operational capability may include providing for the use of multiple remote devices for a single patient with a physical condition so that the patient is not constrained to using a single remote device for medical services.

The process of transacting ongoing business and operational capability may include the use of data associated with a patient using a remote device, the data being transferred via means including but not limited to network transfer from a remote device or data transferred from an internet website; for research purposes including the building of databases of patient information subsequently used for statistical comparison related to diagnosis and assessment of a physical condition.

The process of transacting ongoing business and operational capability may include assessment at a center of data associated with providing a therapeutic prescription on a remote device, and may further comprise notifying a physician or similarly qualified person of medical expertise if worsening of symptoms of a physical condition occurs in a patient being treated on a remote device.

The process of transacting ongoing business and operational capability may include assessment at a center of data associated with providing a therapeutic prescription on a remote device for the purpose of assuring that persons associated with providing the therapeutic prescription are performing procedures in accordance with the therapeutic prescription; and may further provide for notification of a physician or similarly qualified person of medical expertise if procedures are not in accordance with the therapeutic prescription.

The process of transacting ongoing business and operational capability may include preventing application of a therapeutic prescription on a remote device unless the therapeutic prescription has been provided by a center.

The process of transacting ongoing business and operational capability may include providing means for a physician or similarly qualified person of medical expertise to indicate concurrence with the parameters of a therapeutic prescription provided by a center.

The process of transacting ongoing business and operational capability may include (1) providing a finite number of licenses, preferably between one and 100, for a providing a therapeutic prescription; (2) using a license when an application of a therapeutic prescription on a patient with a physical condition using a remote device occurs; (3) decrementing the number of licenses available to the patient; (4) and notifying a center and persons associated with a remote device when the number of licenses reaches a preset limit, preferably between zero and ten.

The invention claimed is:

1. A remote medical assessment and therapy management apparatus comprising:
   a first center user interface;
   a first center computer couplable with the first center user interface and configured to display information via the first center user interface sufficient for a user to assess data associated with a human function or condition and for the user to develop a therapeutic prescription comprising parameters for an electrical stimulation signal to be administered to a patient, and further configured to receive therapeutic control inputs from the user specifying parameters for the electrical stimulation signal in accordance with the therapeutic prescription;
   a remote device located remotely from the center and including:
      at least one medical diagnostic instrument configured to acquire biophysical data from a patient,
      at least one medical therapeutic instrument configured to provide a therapy to a patient, the therapy comprising administration of the electrical stimulation signal, and
      a remote computer configured to (i) receive diagnostic signals from the diagnostic instrument, (ii) automatically select the therapeutic prescription provided by the center computer, (iii) transmit therapeutic control signals to the therapeutic instrument, the therapeutic control signals being configured to cause the therapeutic instrument to administer the electrical stimulation signal to the patient in accordance with the electrical stimulation signal parameters specified in the therapeutic prescription, (iv) authenticate the identity of the patient, (v) receive data pertaining to the status of a set of symptoms of the patient, (vi) receive data pertaining to the patient's physical condition, and (vii) report the data to the center computer; and a network interface connected between the first center computer and the remote computer and configured to (i) transmit diagnostic signals from the remote computer to the first center computer, (ii) transmit the therapeutic control signals from the first center computer to the therapeutic instrument via the remote computer, and (iii) communicate the additional data between computers.

2. The apparatus of claim 1 in which the remote device includes a remote user interface operatively coupled to the remote computer, the remote computer being configured to accept data inputs regarding the patient's condition, and communicate the data to the center computer.

3. A method for remote medical assessment and therapy management, the method including the steps of:
  authenticating the identity of a patient;
  assessing a physical condition of at least one patient co-located with a remote device at a remote facility, by acquiring data pertaining to a physical condition of the patient;
  using a remote device computer to input data pertaining to the status of a set of symptoms of the patient;
  transferring the data from a remote device computer to a center computer located at a center remote from the remote facility;
  analyzing at the center the data pertaining to a physical condition of the patient located at a remote facility;
  determining at the center a therapeutic prescription comprising parameters of an electrical stimulation signal to be administered to a patient;
  transferring the therapeutic prescription from the center to the remote device;
  using software on the remote device computer to automatically select the therapeutic prescription provided for the patient by the center computer and administer to the patient an electrical stimulation signal having parameters specified in the therapeutic prescription;
  acquiring additional data including biophysical measures pertaining to the patient's physical condition after providing the therapeutic prescription; and
  using the remote device computer to input and communicate the additional data to the center computer via network connection.

4. The method of claim 3 further including performing an analysis that includes:
  collecting the EEG of a patient using a remote device;
  mathematically analyzing that EEG, and
  making a statistical comparison of the EEG analysis to similar EEG measures in a database of EEG measures of either:
    healthy normal persons, or
    other persons having a common physical condition.

5. The method of claim 3 further including interactions between a center and a remote device for the purpose of treating a physical condition of a patient using the remote device, with the method including the steps of:
  providing therapy to a patient using a remote device and using a therapeutic prescription determined at a center and transferred to the remote device;
  acquiring data pertaining to a physical condition of a patient taken at or near the time of providing therapy to a patient,
  transferring the data from the remote device to the center, performing, at the center, analysis of the data pertaining to a physical condition,
  determining, at the center, a new therapeutic prescription,
    transferring the new therapeutic prescription from the center to the remote device, and
    providing the new therapeutic prescription to the patient using the remote device.

6. The method of claim 3 further including interactions between a center and a remote device for the purpose of treating a physical condition of a patient using the remote device, with the method including the steps of:
  providing therapy to a patient using a remote device and using a therapeutic prescription determined at the center and transferred to a remote device;
  acquiring data pertaining to a physical condition of a patient and taken at or near the time of therapy;
  transferring the data from the remote device to the center;
  performing, at a center, analysis of the data pertaining to a physical condition;
  determining an analysis of changes in the data over time and associating the analysis of changes with progress toward treating the physical condition of the patient using the remote device; and
  transferring the analysis of changes and progress to the remote device.

7. The method of claim 3 further including interactions between a center and a remote device for the purpose of treating a physical condition of a patient using the remote device, the method including the steps of:
  provision of therapy using a remote device;
  further using a therapeutic prescription determined at a center and transferred to the remote device;
  acquisition of data pertaining to a physical condition and taken at or near the time of therapy;
  transferring the data from the remote device to the center, performing analysis of the data pertaining to a physical condition at the center;
  determining an analysis of changes in the data over time; and
  associating the analysis of changes with progress toward treating a physical condition of the patient using the remote device, and transferring the analysis of changes and progress to an internet website.

8. The method of claim 3 further including the steps of:
  establishing initial network communication between a center and a remote device for the purposes of making transactions including those related to providing services selected from the group of services consisting of a medical service, a business service, and a technical support service; and
  enabling such transactions between the center and the remote device by creating a unique remote device identifier associated with the remote device.

9. The method of claim 3 further including the step of determining a therapeutic prescription by analyzing communicated data, including biophysical measures associated with a physical condition, at a center.

10. The method of claim 3 in which the determination of a therapeutic prescription at a center comprises the steps of:

determining if any contraindications exist based on communicated data;
analyzing biophysical measures of a patient with a physical condition for the determination of therapeutic prescription parameters;
creating a data file including at least one of:
the therapeutic prescription parameters,
a use license indicating a number of allowed applications of a therapy for a patient on a remote device,
a user identifier indicating the identity of a person at a location of a remote device; and
a remote device identifier; and
communicating the data file from a center to a remote device via network interface.

11. The method of claim 3 further including the step of using data from a remote device at a center for quality and reliability monitoring associated with providing a medical service on a remote device.

12. The method of claim 3 further including the assessment of EEG data collected by a remote device, the assessment including mathematically analyzing the EEG data using one or more methods selected from the group of methods consisting of: voltage analysis, current analysis, voltage and current analysis, frequency spectrum analysis using Fast Fourier analysis, frequency spectrum analysis using a wavelet analysis method, frequency spectrum analysis using absolute power analysis method, frequency spectrum analysis using relative power analysis method, frequency spectrum analysis using phase analysis method, frequency spectrum analysis using coherence analysis method, frequency spectrum analysis using amplitude symmetry analysis method, and localization of electrical activity in the brain using inverse EEG computation analysis.

13. The method of claim 4 further including determination of a therapeutic prescription based on the EEG analysis.

14. The method of claim 3 further including the provision and use of an internet website that provides information and data to a physician or similarly qualified person of medical expertise about a physical condition of a patient using a remote device.

15. The method of claim 3 further including the provision and use of an internet website that provides information and data to a person using a remote device for treatment of a physical condition.

16. The method of claim 3 in which the step of acquiring data pertaining to a physical condition of the patient includes acquiring data selected from the data categories consisting of history data, overall health data, and other data that may be a factor in the pathology of a physical condition.

17. The method of claim 3 further including the step of acquiring data about a patient with a physical condition using an internet website.

18. The method of claim 3 further including the steps of:
transmitting data about a patient with a physical condition to a center for analysis; and
using the analysis for one or more purposes selected from the group of purposes consisting of supporting a first diagnosis, providing evidence for a differential diagnosis, and discovering contraindications to the use of a remote device for providing a therapeutic prescription.

19. The method of claim 3 further including the step of transmitting information supporting a first diagnosis or providing evidence for a differential diagnosis from a center to a physician or similarly qualified person of medical expertise for use in the overall treatment of a patient with a physical condition.

20. The method of claim 3 further including the steps of:
discovering contraindications to the use of a remote device for providing a therapeutic prescription to a patient; and
transmitting information to the remote device preventing a therapeutic prescription from being delivered to the patient.

21. The method of claim 3 further including the steps of:
determining whether contraindications to the provision of a therapeutic prescription to a patient have been detected;
determining whether requisite information for providing such therapeutic prescription is present; and
allowing the use of a remote device for providing a therapeutic prescription to the patient only if no contraindications are detected and if the requisite information is present.

22. The method of claim 3 further including the steps of:
establishing communication between a person at a center and a person at a location of a remote device; and
making one or more transactions between the person at the center and the person at the remote device, selected from the group of transactions consisting of providing a medical service, providing a business service, providing a financial service, and providing a technical support service.

23. The method of claim 3 further including the step of creating a user account for a patient with a physical condition on a remote device, the user account to include the patient's name, a unique user number, information related to providing medical services including assessing and treating a physical condition, and history information associated with assessing and treating a physical condition.

24. The method of claim 3 further including the step of authenticating that a patient using a remote device for provision of medical services is the same as a person bearing a certain user name and account.

25. The method of claim 10 in which:
the step of creating a data file includes creating a data file that includes a use license indicating a number of allowed applications of a therapy for a patent on a remote device;
the method further includes the step of determining whether a number of allowed applications remaining in the use license is greater than zero; and
if the number of allowed applications remaining is greater than zero, executing the step of using the remote device to administer to the patient an electrical stimulation signal having parameters specified in the therapeutic prescription.

26. The method of claim 3 further including the use of multiple remote devices to apply electrical stimulation signals to a single patient having a physical condition.

27. The method of claim 3 in which:
the step of transferring the data includes receiving the data from the remote device via network connection;
the analyzing step includes:
performing a mathematical analysis and a statistical analysis on the data, and
using the mathematical and statistical analyses to quantify the status of symptoms associated with a physical condition;
the determining step includes using the mathematical and statistical analyses to create a new therapeutic prescription; and following the determining step, the method includes the additional step of communicating the therapeutic prescription to an internet website accessible to a qualified person.

28. The method of claim 3 including, following the step of using the remote device to administer to the patient an electrical stimulation, the additional steps of:
assessing, at the center, data associated with changes in patient condition, and
notifying a qualified person of medical expertise of the changes in patient condition.

29. The method of claim 3 further including the steps of:
determining at the center a prescribed number of therapeutic prescription applications to be provided the patient at the remote location;
creating an account for the patient including a number of licenses equal to the prescribed number of therapeutic prescription applications prescribed;
decrementing the number of licenses available to the patient before the step of using the remote device to administer to the patient an electrical stimulation signal; and
notifying a remote device operator when the number of licenses in the account reaches a predetermined minimum value.

30. A method for remote medical assessment and therapy management, the method including the steps of:
assessing a physical condition of at least one patient co-located with a remote device at a remote facility, by acquiring data pertaining to a physical condition of the patient;
transferring the data from a remote device to a center computer located at a center remote from the remote facility via network connection;
analyzing at the center the data pertaining to a physical condition of the patient located at a remote facility, wherein the analysis includes performing a mathematical analysis and a statistical analysis on the data, and using the mathematical and statistical analyses to quantify the status of symptoms associated with a physical condition;
determining at the center a therapeutic prescription comprising parameters of an electrical stimulation signal to be administered to a patient, wherein the determination is made using the mathematical and statistical analyses;
transferring the therapeutic prescription from the center to the remote device; and
using the remote device to administer to the patient an electrical stimulation signal having parameters specified in the therapeutic prescription.

31. The method of claim 30 further including performing an analysis that includes:
collecting the EEG of a patient using a remote device;
mathematically analyzing that EEG, and
making a statistical comparison of the EEG analysis to similar EEG measures in a database of EEG measures of either:
healthy normal persons, or
other persons having a common physical condition.

32. The method of claim 30 further including interactions between a center and a remote device for the purpose of treating a physical condition of a patient using the remote device, with the method including the steps of:
providing therapy to a patient using a remote device and using a therapeutic prescription determined at a center and transferred to the remote device;
acquiring data pertaining to a physical condition of a patient taken at or near the time of providing therapy to a patient,
transferring the data from the remote device to the center,
performing, at the center, analysis of the data pertaining to a physical condition,
determining, at the center, a new therapeutic prescription,
transferring the new therapeutic prescription from the center to the remote device, and
providing the new therapeutic prescription to the patient using the remote device.

33. The method of claim 30 further including interactions between a center and a remote device for the purpose of treating a physical condition of a patient using the remote device, with the method including the steps of:
providing therapy to a patient using a remote device and using a therapeutic prescription determined at the center and transferred to a remote device;
acquiring data pertaining to a physical condition of a patient and taken at or near the time of therapy;
transferring the data from the remote device to the center;
performing, at a center, analysis of the data pertaining to a physical condition;
determining an analysis of changes in the data over time and associating the analysis of changes with progress toward treating the physical condition of the patient using the remote device; and
transferring the analysis of changes and progress to the remote device.

34. The method of claim 30 further including interactions between a center and a remote device for the purpose of treating a physical condition of a patient using the remote device, the method including the steps of:
provision of therapy using a remote device;
further using a therapeutic prescription determined at a center and transferred to the remote device;
acquisition of data pertaining to a physical condition and taken at or near the time of therapy;
transferring the data from the remote device to the center,
performing analysis of the data pertaining to a physical condition at the center;
determining an analysis of changes in the data over time; and
associating the analysis of changes with progress toward treating a physical condition of the patient using the remote device, and transferring the analysis of changes and progress to an internet website.

35. The method of claim 30 further including the step of determining a therapeutic prescription by analyzing communicated data, including biophysical measures associated with a physical condition, at a center.

36. The method of claim 30 in which the determination of a therapeutic prescription at a center comprises the steps of:
determining if any contraindications exist based on communicated data;
analyzing biophysical measures of a patient with a physical condition for the determination of therapeutic prescription parameters;
creating a data file including at least one of:
the therapeutic prescription parameters,
a use license indicating a number of allowed applications of a therapy for a patient on a remote device,
a user identifier indicating the identity of a person at a location of a remote device; and
a remote device identifier; and
communicating the data file from a center to a remote device via network interface.

37. The method of claim 30 further including the step of using data from a remote device at a center for quality and reliability monitoring associated with providing a medical service on a remote device.

38. The method of claim 30 further including the assessment of EEG data collected by a remote device, the assessment including mathematically analyzing the EEG data using one or more methods selected from the group of methods consisting of: voltage analysis, current analysis, voltage and current analysis, frequency spectrum analysis using Fast Fourier analysis, frequency spectrum analysis using a wavelet analysis method, frequency spectrum analysis using absolute power analysis method, frequency spectrum analysis using relative power analysis method, frequency spectrum analysis using phase analysis method, frequency spectrum analysis using coherence analysis method, frequency spectrum analysis using amplitude symmetry analysis method, and localization of electrical activity in the brain using inverse EEG computation analysis.

39. The method of claim 38 further including determination of a therapeutic prescription based on the EEG analysis.

40. The method of claim 30 further including the provision and use of an internet website that provides information and data to a physician or similarly qualified person of medical expertise about a physical condition of a patient using a remote device.

41. The method of claim 30 further including the provision and use of an internet website that provides information and data to a person using a remote device for treatment of a physical condition.

42. The method of claim 30 in which the step of acquiring data about a patient includes acquiring data selected from the data categories consisting of history data, overall health data, and other data that may be a factor in the pathology of a physical condition.

43. The method of claim 30 further including the step of acquiring data about a patient with a physical condition using an internet website.

44. The method of claim 30 further including the steps of:
transmitting data about a patient with a physical condition to a center for analysis; and
using the analysis for one or more purposes selected from the group of purposes consisting of supporting a first diagnosis, providing evidence for a differential diagnosis, and discovering contraindications to the use of a remote device for providing a therapeutic prescription.

45. The method of claim 30 further including the step of transmitting information supporting a first diagnosis or providing evidence for a differential diagnosis from a center to a physician or similarly qualified person of medical expertise for use in the overall treatment of a patient with a physical condition.

46. The method of claim 30 further including the steps of:
discovering contraindications to the use of a remote device for providing a therapeutic prescription to a patient; and
transmitting information to the remote device preventing a therapeutic prescription from being delivered to the patient.

47. The method of claim 30 further including the steps of:
determining whether contraindications to the provision of a therapeutic prescription to a patient have been detected;
determining whether requisite information for providing such therapeutic prescription is present; and
allowing the use of a remote device for providing a therapeutic prescription to the patient only if no contraindications are detected and if the requisite information is present.

48. The method of claim 30 further including the steps of:
establishing communication between a person at a center and a person at a location of a remote device; and
making one or more transactions between the person at the center and the person at the remote device, selected from the group of transactions consisting of providing a medical service, providing a business service, providing a financial service, and providing a technical support service.

49. The method of claim 30 further including the step of creating a user account for a patient with a physical condition on a remote device, the user account to include the patient's name, a unique user number, information related to providing medical services including assessing and treating a physical condition, and history information associated with assessing and treating a physical condition.

50. The method of claim 30 further including the step of authenticating that a patient using a remote device for provision of medical services is the same as a person bearing a certain user name and account.

51. The method of claim 30 in which:
the step of creating a data file includes creating a data file that includes a use license indicating a number of allowed applications of a therapy for a patent on a remote device;
the method further includes the step of determining whether a number of allowed applications remaining in the use license is greater than zero; and
if the number of allowed applications remaining is greater than zero, executing the step of using the remote device to administer to the patient an electrical stimulation signal having parameters specified in the therapeutic prescription.

52. The method of claim 30 further including the use of multiple remote devices to apply electrical stimulation signals to a single patient having a physical condition.

53. The method of claim 30 further in which:
the step of acquiring data pertaining to a physical condition of the patient includes the steps of:
authenticating the identity of the patient; and
using a remote device computer to input data pertaining to the status of a set of symptoms of the patient;
the step of transferring the data includes using the remote device computer to report the data to the center computer;
the step of using the remote device includes using software running on the remote device computer to automatically select the therapeutic prescription provided for the patient by the center computer; and
after providing the therapeutic prescription, the method includes the additional steps of:
acquiring additional data including biophysical measures pertaining to the patient's physical condition, and
using the remote device computer to input and communicate the additional data to the center computer via network connection.

54. The method of claim 30 including, following the step of using the remote device to administer to the patient an electrical stimulation, the additional steps of:
assessing, at the center, data associated with changes in patient condition, and notifying a qualified person of medical expertise of the changes in patient condition.

55. The method of claim 30 further including the steps of:
determining at the center a prescribed number of therapeutic prescription applications to be provided the patient at the remote location;
creating an account for the patient including a number of licenses equal to the prescribed number of therapeutic prescription applications prescribed;
decrementing the number of licenses available to the patient before the step of using the remote device to administer to the patient an electrical stimulation signal; and
notifying a remote device operator when the number of licenses in the account reaches a predetermined minimum value.

56. A method for remote medical assessment and therapy management, the method including the steps of:
assessing a physical condition of at least one patient co-located with a remote device at a remote facility, by acquiring data pertaining to a physical condition of the patient;
transferring the data from a remote device to a center computer located at a center remote from the remote facility;
analyzing at the center the data pertaining to a physical condition of the patient located at a remote facility;
determining at the center a therapeutic prescription comprising parameters of an electrical stimulation signal and a prescribed number of therapeutic prescription applications to be provided the patient at the remote location;
creating an account for the patient including a number of licenses equal to the prescribed number of therapeutic prescription applications prescribed;
transferring the therapeutic prescription from the center to the remote device; using the remote device to administer to the patient an electrical stimulation signal having parameters specified in the therapeutic prescription;
decrementing the number of licenses available to the patient; and
notifying a remote device operator when the number of licenses in the account reaches a predetermined minimum value.

57. The method of claim 56 further including performing an analysis that includes:
collecting the EEG of a patient using a remote device;
mathematically analyzing that EEG, and
making a statistical comparison of the EEG analysis to similar EEG measures in a database of EEG measures of either:
healthy normal persons, or
other persons having a common physical condition.

58. The method of claim 56 further including interactions between a center and a remote device for the purpose of treating a physical condition of a patient using the remote device, with the method including the steps of:
providing therapy to a patient using a remote device and using a therapeutic prescription determined at a center and transferred to the remote device;
acquiring data pertaining to a physical condition of a patient taken at or near the time of providing therapy to a patient,
transferring the data from the remote device to the center, performing, at the center, analysis of the data pertaining to a physical condition,
determining, at the center, a new therapeutic prescription,
transferring the new therapeutic prescription from the center to the remote device, and
providing the new therapeutic prescription to the patient using the remote device.

59. The method of claim 56 further including interactions between a center and a remote device for the purpose of treating a physical condition of a patient using the remote device, with the method including the steps of:
providing therapy to a patient using a remote device and using a therapeutic prescription determined at the center and transferred to a remote device;
acquiring data pertaining to a physical condition of a patient and taken at or near the time of therapy;
transferring the data from the remote device to the center;
performing, at a center, analysis of the data pertaining to a physical condition;
determining an analysis of changes in the data over time and associating the analysis of changes with progress toward treating the physical condition of the patient using the remote device; and
transferring the analysis of changes and progress to the remote device.

60. The method of claim 56 further including interactions between a center and a remote device for the purpose of treating a physical condition of a patient using the remote device, the method including the steps of:
provision of therapy using a remote device;
further using a therapeutic prescription determined at a center and transferred to the remote device;
acquisition of data pertaining to a physical condition and taken at or near the time of therapy;
transferring the data from the remote device to the center, performing analysis of the data pertaining to a physical condition at the center;
determining an analysis of changes in the data over time; and
associating the analysis of changes with progress toward treating a physical condition of the patient using the remote device, and transferring the analysis of changes and progress to an internet website.

61. The method of claim 56 further including the steps of:
establishing initial network communication between a center and a remote device for the purposes of making transactions including those related to providing services selected from the group of services consisting of a medical service, a business service, and a technical support service; and
enabling such transactions between the center and the remote device by creating a unique remote device identifier associated with the remote device.

62. The method of claim 56 further including the step of determining a therapeutic prescription by analyzing communicated data, including biophysical measures associated with a physical condition, at a center.

63. The method of claim 56 in which the determination of a therapeutic prescription at a center comprises the steps of:
determining if any contraindications exist based on communicated data;
analyzing biophysical measures of a patient with a physical condition for the determination of therapeutic prescription parameters;
creating a data file including at least one of:
the therapeutic prescription parameters,
a use license indicating a number of allowed applications of a therapy for a patient on a remote device, a user identifier indicating the identity of a person at a location of a remote device; and
a remote device identifier; and
communicating the data file from a center to a remote device via network interface.

64. The method of claim 56 further including the step of using data from a remote device at a center for quality and reliability monitoring associated with providing a medical service on a remote device.

65. The method of claim 56 further including the assessment of EEG data collected by a remote device, the assessment including mathematically analyzing the EEG data using one or more methods selected from the group of methods consisting of: voltage analysis, current analysis, voltage and current analysis, frequency spectrum analysis using Fast Fourier analysis, frequency spectrum analysis using a wavelet analysis method, frequency spectrum analysis using absolute power analysis method, frequency spectrum analysis using relative power analysis method, frequency spectrum analysis using phase analysis method, frequency spectrum analysis using coherence analysis method, frequency spectrum analysis using amplitude symmetry analysis method, and localization of electrical activity in the brain using inverse EEG computation analysis.

66. The method of claim 65 further including determination of a therapeutic prescription based on the EEG analysis.

67. The method of claim 56 further including the provision and use of an internet website that provides information and data to a physician or similarly qualified person of medical expertise about a physical condition of a patient using a remote device.

68. The method of claim 56 further including the provision and use of an internet website that provides information and data to a person using a remote device for treatment of a physical condition.

69. The method of claim 56 in which the step of acquiring data about a patient includes acquiring data selected from the data categories consisting of history data, overall health data, and other data that may be a factor in the pathology of a physical condition.

70. The method of claim 56 further including the step of acquiring data about a patient with a physical condition using an internet website.

71. The method of claim 56 further including the steps of:
transmitting data about a patient with a physical condition to a center for analysis; and
using the analysis for one or more purposes selected from the group of purposes consisting of supporting a first diagnosis, providing evidence for a differential diagnosis, and discovering contraindications to the use of a remote device for providing a therapeutic prescription.

72. The method of claim 56 further including the step of transmitting information supporting a first diagnosis or providing evidence for a differential diagnosis from a center to a physician or similarly qualified person of medical expertise for use in the overall treatment of a patient with a physical condition.

73. The method of claim 56 further including the steps of:
discovering contraindications to the use of a remote device for providing a therapeutic prescription to a patient; and
transmitting information to the remote device preventing a therapeutic prescription from being delivered to the patient.

74. The method of claim 56 further including the steps of:
determining whether contraindications to the provision of a therapeutic prescription to a patient have been detected;
determining whether requisite information for providing such therapeutic prescription is present; and
allowing the use of a remote device for providing a therapeutic prescription to the patient only if no contraindications are detected and if the requisite information is present.

75. The method of claim 56 further including the steps of:
establishing communication between a person at a center and a person at a location of a remote device; and
making one or more transactions between the person at the center and the person at the remote device, selected from the group of transactions consisting of providing a medical service, providing a business service, providing a financial service, and providing a technical support service.

76. The method of claim 56 further including the step of creating a user account for a patient with a physical condition on a remote device, the user account to include the patient's name, a unique user number, information related to providing medical services including assessing and treating a physical condition, and history information associated with assessing and treating a physical condition.

77. The method of claim 56 further including the step of authenticating that a patient using a remote device for provision of medical services is the same as a person bearing a certain user name and account.

78. The method of claim 63 in which:
the step of creating a data file includes creating a data file that includes a use license indicating a number of allowed applications of a therapy for a patent on a remote device;
the method further includes the step of determining whether a number of allowed applications remaining in the use license is greater than zero; and
if the number of allowed applications remaining is greater than zero, executing the step of using the remote device to administer to the patient an electrical stimulation signal having parameters specified in the therapeutic prescription.

79. The method of claim 56 further including the use of multiple remote devices to apply electrical stimulation signals to a single patient having a physical condition.

80. The method of claim 56 further in which:
the step of acquiring data pertaining to a physical condition of the patient includes the steps of:
authenticating the identity of the patient; and
using a remote device computer to input data pertaining to the status of a set of symptoms of the patient;
the step of transferring the data includes using the remote device computer to report the data to the center computer;
the step of using the remote device includes using software running on the remote device computer to automatically select the therapeutic prescription provided for the patient by the center computer; and
after providing the therapeutic prescription, the method includes the additional steps of:
acquiring additional data including biophysical measures pertaining to the patient's physical condition, and
using the remote device computer to input and communicate the additional data to the center computer via network connection.

81. The method of claim 56 in which:
the step of transferring the data includes receiving the data from the remote device via network connection;

the analyzing step includes:
   performing a mathematical analysis and a statistical analysis on the data, and
   using the mathematical and statistical analyses to quantify the status of symptoms associated with a physical condition;
the determining step includes using the mathematical and statistical analyses to create a new therapeutic prescription; and
following the determining step, the method includes the additional step of communicating the therapeutic prescription to an internet website accessible to a qualified person.

82. The method of claim 56 including, following the step of using the remote device to administer to the patient an electrical stimulation, the additional steps of:
   assessing, at the center, data associated with changes in patient condition, and
   notifying a qualified person of medical expertise of the changes in patient condition.

* * * * *

UNITED STATES PATENT AND TRADEMARK OFFICE
CERTIFICATE OF CORRECTION

PATENT NO. : 8,849,681 B2  
APPLICATION NO. : 12/672509  
DATED : September 30, 2014  
INVENTOR(S) : Hargrove et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 376 days.

Signed and Sealed this  
Twentieth Day of October, 2015

Michelle K. Lee  
*Director of the United States Patent and Trademark Office*